United States Patent
Kim (10) Patent No.: US 11,628,045 B2
(45) Date of Patent: Apr. 18, 2023

(54) TORQUE WRENCH FOR IMPLANT PROCEDURE

(71) Applicant: Denflex Co., LTD, Seoul (KR)

(72) Inventor: Hyung-Woo Kim, Gyeonggi-do (KR)

( * ) Notice: Subject to any disclaimer, the term of this patent is extended or adjusted under 35 U.S.C. 154(b) by 321 days.

(21) Appl. No.: 16/832,662

(22) Filed: Mar. 27, 2020

(65) Prior Publication Data

US 2020/0323612 A1  Oct. 15, 2020

Related U.S. Application Data (63) Continuation of application No. PCT/KR2020/002672, filed on Feb. 25, 2020.

(30) Foreign Application Priority Data

Apr. 10, 2019 (KR) .................. 10-2019-0041977
Nov. 25, 2019 (KR) .................. 10-2019-0152000

(51) Int. Cl.
| | | |
|---|---|---|
| *A61C 8/00* | (2006.01) | |
| *A61B 17/88* | (2006.01) | |
| *B25B 23/142* | (2006.01) | |
| *A61C 1/18* | (2006.01) | |
| *A61B 90/00* | (2016.01) | |

(52) U.S. Cl.
CPC ........ *A61C 8/0089* (2013.01); *A61B 17/8875* (2013.01); *A61C 1/186* (2013.01); *B25B 23/1427* (2013.01); *A61B 2090/066* (2016.02)

(58) Field of Classification Search
CPC ....... A61C 8/00; A61C 8/0089; A61C 8/0095; A61C 8/0096; A61C 8/0098; A61C 1/18; A61C 1/186; A61C 3/00; A61C 1/14; A61B 17/00; A61B 17/88; A61B 17/8875; A61B 2090/066; B25B 17/00; B25B 23/14; B25B 23/142; B25B 23/1427; B25B 23/145; B25B 23/147
See application file for complete search history.

(56) References Cited

U.S. PATENT DOCUMENTS

| | | | | |
|---|---|---|---|---|
| 3,733,936 A | * | 5/1973 | Flynn | ...................... B25B 17/00 81/57.29 |
| 5,626,474 A | * | 5/1997 | Kukla | .................. A61C 8/0089 81/146 |

(Continued)

FOREIGN PATENT DOCUMENTS

| | | |
|---|---|---|
| KR | 20-0300718 A | 1/2003 |
| KR | 10-0948726 A | 3/2010 |
| KR | 20-2014-0003885 | 6/2014 |

*Primary Examiner* — Robert J Scruggs (57) ABSTRACT

Provided is a torque wrench for an implant procedure including: a first body having a predetermined length, and including a head portion having an end to which a torque wrench driver bit is coupled; at least one second body having a predetermined length, provided at one side of the first body, and including a coupling portion formed in a longitudinal direction thereof; and a second shaft rotatably coupled to the coupling portion of the second body, including a second gear provided at one end thereof and a knob provided at the other end thereof, and configured such that, in response to rotation of the knob, the second shaft transmits torque to the torque wrench driver bit through the first gear engaged with the second gear.

7 Claims, 5 Drawing Sheets

(56) References Cited

U.S. PATENT DOCUMENTS

| | | | | |
|---|---|---|---|---|
| 5,734,113 A | * | 3/1998 | Vogt | A61B 17/8875 |
| | | | | 73/862.21 |
| 9,539,043 B2 | * | 1/2017 | DeFalco | A61B 17/8875 |
| 2007/0281274 A1 | * | 12/2007 | Schraffran | A61C 8/0089 |
| | | | | 433/141 |

* cited by examiner

TORQUE WRENCH FOR IMPLANT PROCEDURE

CROSS-REFERENCE TO EARLIER FILED APPLICATIONS

The present application is a continuation of and claims the benefit of PCT/KR2020/002672 filed Feb. 25, 2020, which claims the benefit of foreign application KR 10-2019-0152000 filed Nov. 25, 2019 and KR 10-2019-0041977 filed Apr. 10, 2019, the entire disclosures of which are hereby incorporated by reference.

FIELD OF THE INVENTION

The present invention relates generally to a torque wrench for an implant procedure. More particularly, the present invention relates to a torque wrench for an implant procedure, wherein only a single torque wrench according to the present invention is necessary to first tighten a screw and finally firmly fasten the screw with a desired force or to first loosen the screw and finally completely remove the screw, even without the use of a separate hand driver.

BACKGROUND OF THE INVENTION

An implant denotes a replacement for restoring lost human tissue. In the field of dentistry, the implant in general denotes a replacement that is used to restore the original function of a tooth by implanting and adhering a fixture in an alveolar bone from which a root of a natural tooth has been lost, connecting an abutment to the top of the fixture, and fixing a crown on the abutment.

As such an implant for a dental implant procedure, the most common is a screw-type, in which an abutment and a fixture are fastened together by means of clamping force of a screw. This screw-type implant is composed of a fixture, an abutment, and a prosthesis.

In the procedure for the screw-type implant, in a conventional method, fastening or unfastening of the fixture and the abutment with the screw is performed by using both a separate hand driver and a conventional torque wrench for implant procedures that can firmly tighten a screw with a specific torque.

When fastening or unfastening with a screw using the conventional torque wrench, the torque wrench can be used only after a male screw is engaged to a corresponding female screw. In particular, when the male screw is tightened with the torque wrench in a state in which the male screw and the female screw are not engaged or are not fully engaged, there is a problem in that the torque wrench may not rotate properly and fail to fasten the screws. Due to this problem, when fastening with a screw, the screw has to be first tightened to a certain degree with the separate hand driver rather than the torque wrench, and then firmly tightened again with the torque wrench to prevent the screw from being loosened due to continuously applied masticatory pressure. Likewise, when loosening the firmly tightened screw, the screw has to be loosened with the torque wrench to a certain degree, and then finally the hand driver has to be used again for complete removal, which is a cumbersome process.

During a dental implant procedure, when a fastening site where an abutment and a fixture are fastened is located deep inside the oral cavity, an operator first has to tighten a screw to a certain degree with the hand driver in one hand while opening a patient's mouth with the other hand, and then the hand driver has to be replaced with the torque wrench to firmly tighten the screw with a high torque. In particular, in the case of a patient whose mouth is hard to open, it may not easy to accurately position and tighten the hand driver directly on the fastening site in the oral cavity. In some cases, the operator may accidentally drop the driver in the oral cavity.

SUMMARY OF THE INVENTION

Accordingly, the present invention has been made keeping in mind the above problems occurring in the related art, and an objective of the present invention is to provide a torque wrench, wherein only a single torque wrench according to the present invention is necessary to first tighten a screw and finally firmly fasten the screw with a desired force or to first loosen the screw and finally completely remove the screw, even without the use of a separate hand driver, thereby making it possible to reduce discomfort that a patient has to open his/her mouth excessively during a procedure, or that an operator needs to use his/her hand to tighten the screw at a site where access is difficult.

Another objective of the present invention is to provide a torque wrench that is configured to enable a screw to be efficiently fastened and removed with only a single torque wrench, thereby enabling a more precise and stable procedure, as well as shortening a procedure time.

Still another objective of the present invention is to provide a torque wrench capable of eliminating cumbersome operation of having to provide a hand driver and a torque wrench at the same time and having to exchange the driver for the wrench during a procedure of fastening or removing a screw.

Still another objective of the present invention is to provide a torque wrench that does not require the use of a hand driver, thereby preventing the problem that a patient may swallow the hand driver.

In order to accomplish the above objective, according to one aspect of the present invention, there is provided a torque wrench for an implant procedure, the torque wrench including: a first body part having a predetermined length, and including a head portion having an end to which a torque wrench driver bit is coupled; at least one second body part having a predetermined length, provided at one side of the first body part, and including a coupling portion formed in a longitudinal direction thereof; and a second shaft rotatably coupled to the coupling portion of the second body part, including a second gear provided at one end thereof and a knob provided at the other end thereof, and configured such that, in response to rotation of the knob, the second shaft transmits torque to the torque wrench driver bit through the first gear engaged with the second gear.

Preferably, the first gear may be rotatably provided at an upper side of the torque wrench driver bit or at one side of the head portion of the first body part.

More preferably, the first gear may be provided at an upper end of a rotor inserted into the fastening hole formed in the head portion, and a plurality of ratchet grooves may be formed in an outer surface of the rotor.

Most preferably, the torque wrench may further include a bar-shaped torque gauge provided at one side of the first body part.

Preferably, the torque wrench may further include a protective cover protecting a portion where the first gear and the second gear are engaged with each other from being exposed externally.

According to the present invention, the following effects are provided.

First, it is possible to first tighten the screw and finally firmly fasten the screw or to loosen the screw and completely remove the screw by using only a single torque wrench according to the present invention, even without the use of a separate hand driver. This makes it possible to prevent the problem that an operator may accidentally drop the driver and a patient may swallow the driver during a procedure.

Second, the present invention is configured to enable a screw to be efficiently fastened and removed with only a single torque wrench, thereby enabling a more precise and stable procedure, as well as to shortening a procedure time.

Third, it is possible to eliminate cumbersome operation of having to provide a hand driver and a torque wrench at the same time and having to exchange the driver for the wrench during a procedure of fastening or removing a screw.

DETAILED DESCRIPTION OF THE INVENTION

Hereinafter, exemplary embodiments of the present invention will be described in more detail with reference to the accompanying drawings.

Figure 1:
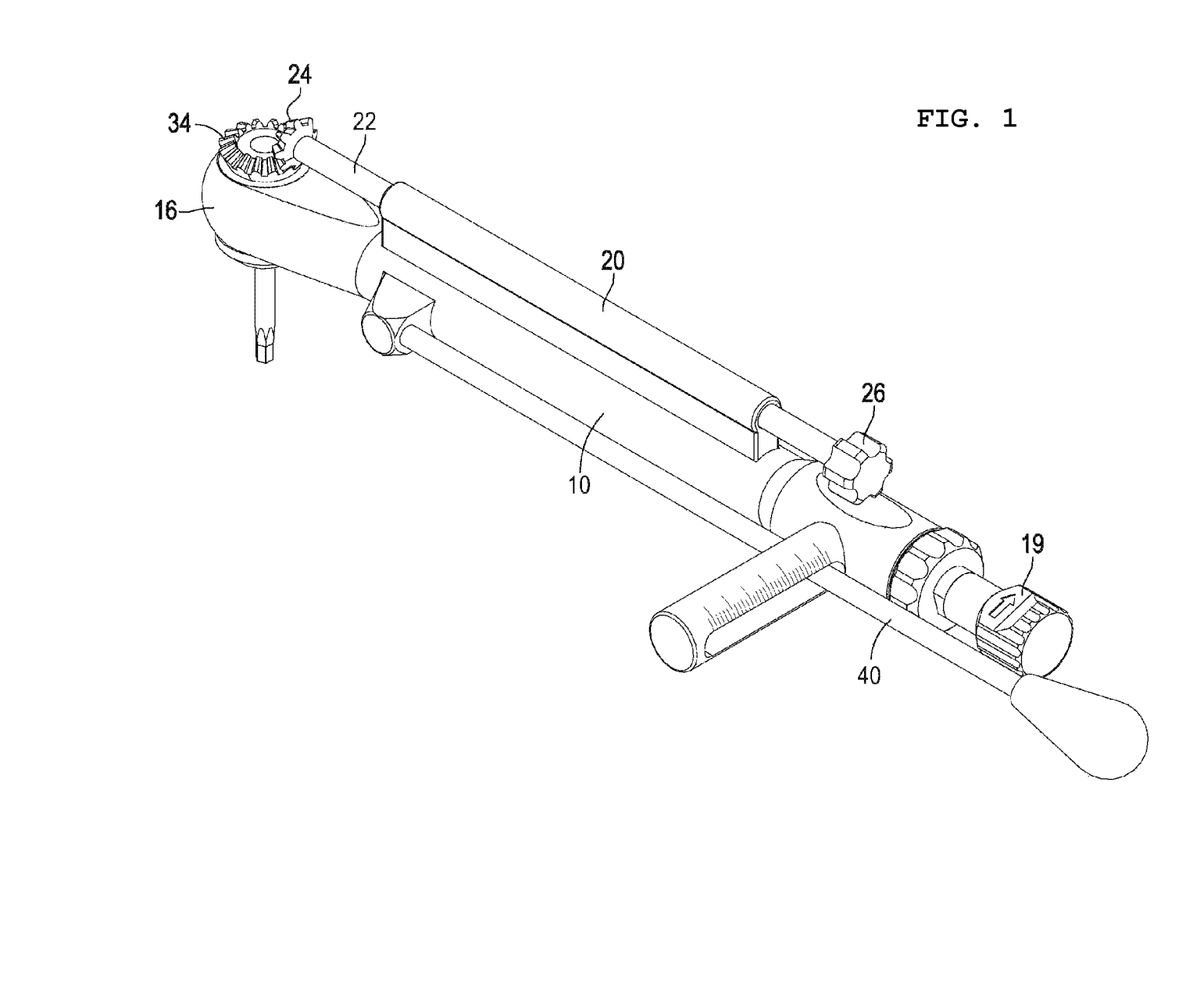
FIG. 1 is a perspective view illustrating a torque wrench according to an embodiment of the present invention.
Figure 2:
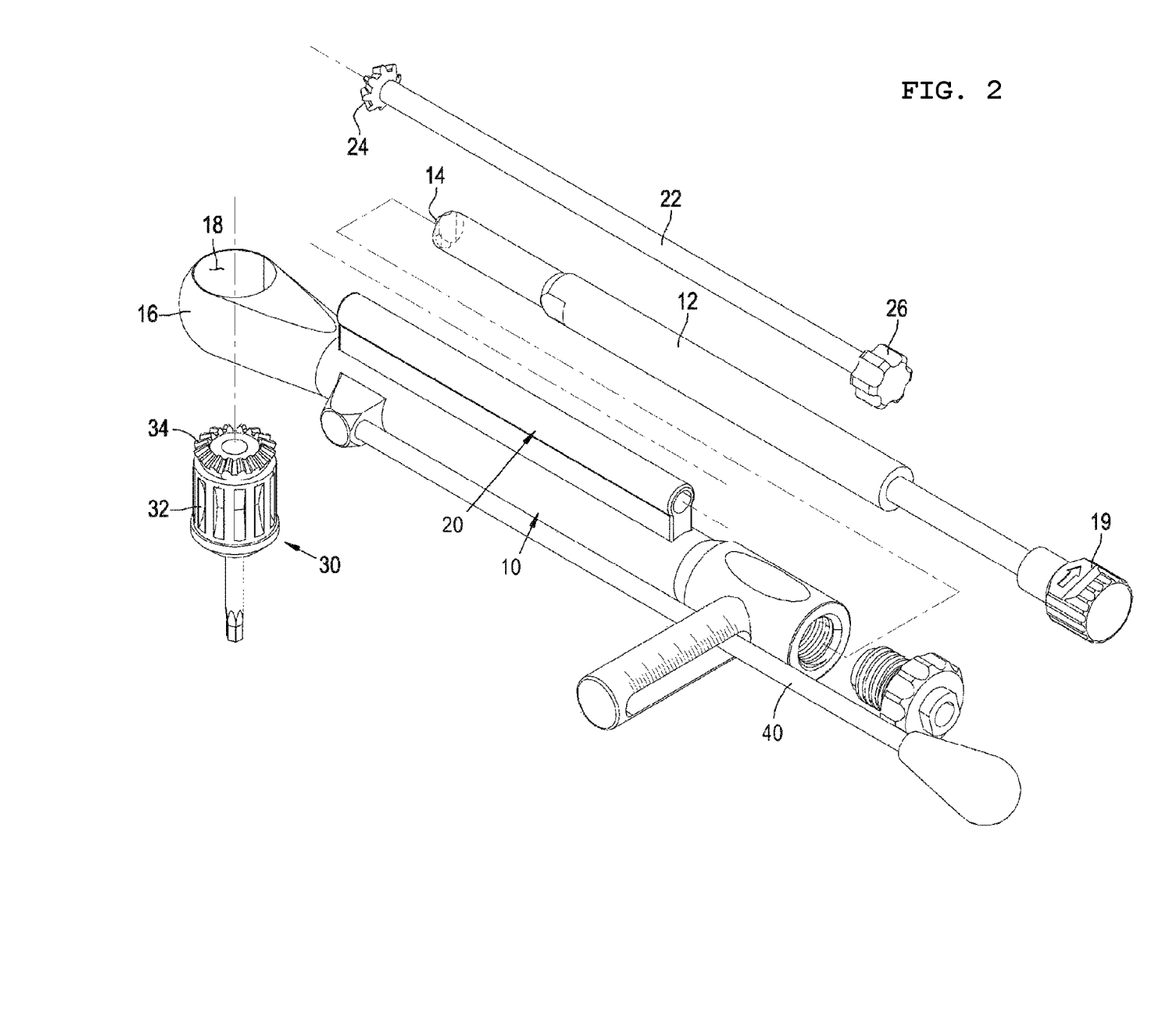
FIG. 2 is an exploded perspective view illustrating the torque wrench according to the embodiment of the present invention.

FIG. 1 is a perspective view illustrating a torque wrench according to an embodiment of the present invention, and FIG. 2 is an exploded perspective view illustrating the torque wrench according to the embodiment of the present invention. Referring to FIGS. 1 and 2, a torque wrench for an implant procedure according to an embodiment of the present invention includes: a first body part 10 having a predetermined length, and including a head portion 16 in which a fastening hole 18 is formed at an end thereof to allow a torque wrench driver bit 30 to be detachably coupled thereto; at least one second body part 20 having a predetermined length, provided at one side of the first body part 10, and including a coupling portion formed in a longitudinal direction thereof; and a second shaft 22 rotatably coupled to the coupling portion of the second body part 20, including a second gear 24 provided at one end thereof and a knob 26 provided at the other end thereof, and configured such that, in response to rotation of the knob 26, the second shaft transmits torque to the torque wrench driver bit 30 through the first gear 34 engaged with the second gear 24.

As illustrated in FIG. 2, the first body part 10 includes the head portion 16 in which the fastening hole 18 is formed at one end thereof, and the fastening hole 18 of the head portion 16 allows the torque wrench driver bit 30 to be detachably coupled thereto. The first body part 10 may be configured such that the torque wrench driver bit is rotatable only in one direction by the operation of rotation direction control knobs 19 and 199.

The at least one second body part 20 is provided at one side of the first body part 10 at a predetermined length along a longitudinal direction of the first body part 10, with the coupling portion formed in the longitudinal direction thereof. Here, the coupling portion may be implemented in any form to which the second shaft can be rotatably coupled, preferably in the form of a hollow portion, and may be configured such that one side between opposite ends thereof is open externally.

Figure 3:
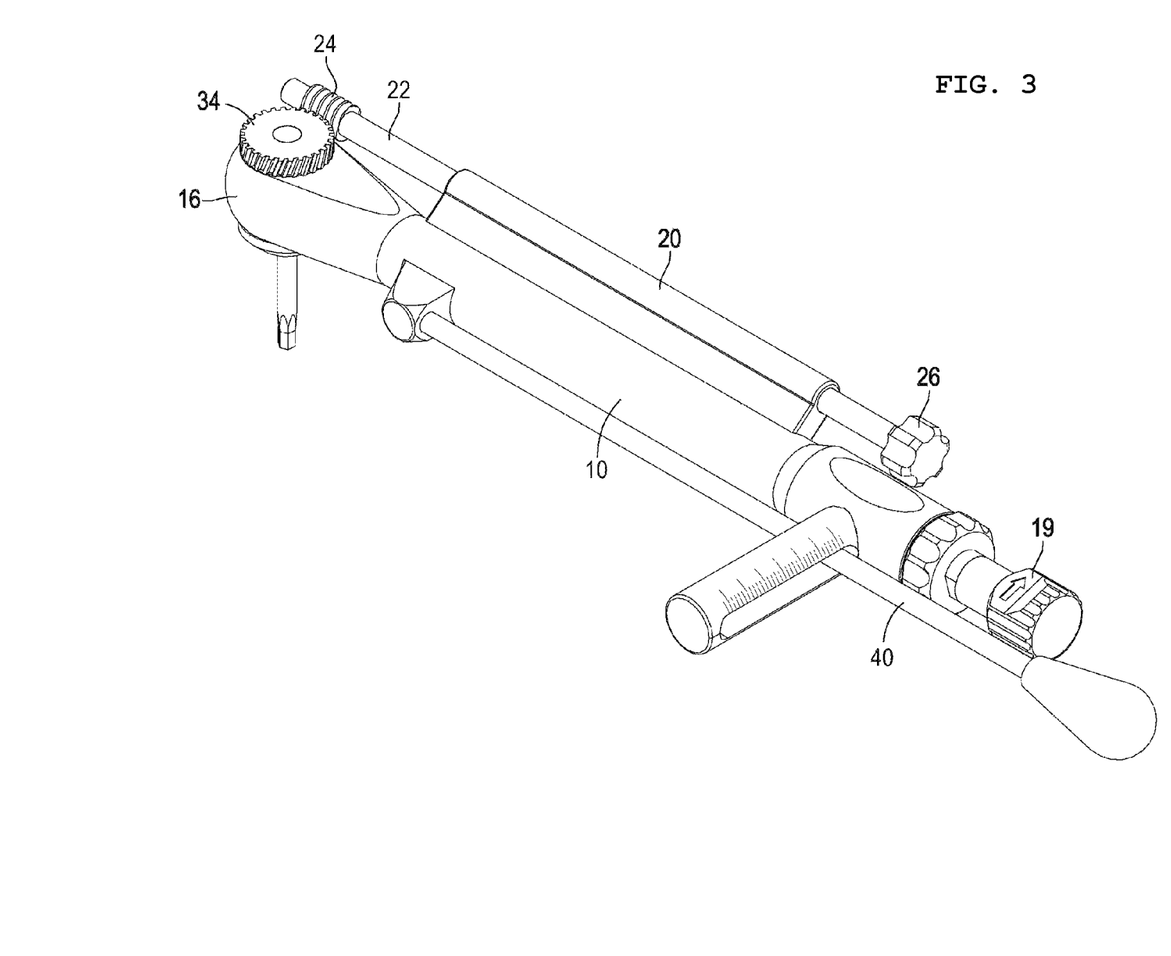
FIG. 3 is a perspective view illustrating a torque wrench according to another embodiment of the present invention.

The second shaft 22 is coupled to the coupling portion of the second body part 20, and is configured such that, in response to rotation of the knob 26 provided at the other end thereof, the second shaft transmits torque to the torque wrench driver bit 30 fastened to the fastening hole 18, through the second gear 24 formed at the end of the second shaft 22 and the first gear 34 engaged with the second gear 24. Preferably, the first gear 34 is a first bevel gear, and the second gear 24 is a second bevel gear. In some cases, as illustrated in FIG. 3, the first and second gears may be implemented as worm gears. Meanwhile, FIGS. 1 and 2 illustrate that the first gear 34 is formed at an upper end of the torque wrench driver bit 30, but the present invention is not limited thereto. Therefore, it should be interpreted as a concept including a gear with arbitrary position and structure, the gear being capable of transmitting torque to the torque wrench driver bit 30 by engagement with the second gear 24. For example, there may be provided a rotor integrally coupled to the head portion of the first body part 10 so as to be rotatable, and including a first gear formed at an upper end thereof.

Preferably, a hollow portion may be further formed in the first body part 10 in the longitudinal direction thereof, and the first shaft 12 formed such that a ratchet protrusion 14 protrudes at one end thereof is inserted into the hollow portion of the first body part 10, and the ratchet protrusion 14 may be coupled to the torque wrench driver bit 30 so as to transmit torque thereto in one direction.

That is, as illustrated in FIG. 2, a plurality of ratchet grooves 32 are formed in an outer surface of the torque wrench driver bit 30, so that the ratchet protrusion protruding at one end of the first shaft 12 may be coupled to the ratchet grooves 32 to enable one-way torque transmission.

Preferably, the structure and shape of the torque wrench driver bit 30 and the fastening hole 18 may also be variously modified.

More preferably, the other end of the first shaft 12 is provided with the rotation direction control knob 19 that can determine the rotation direction of the torque wrench, and the other end of the second shaft 22 is provided with the knob 26. In some cases, the provision of the rotation direction control knob 19 that can determine the rotation direction of the torque wrench may be eliminated. To change the rotation direction of the torque wrench in the absence of the rotation direction control knob 19, the torque wrench driver bit fastened to the fastening hole of the torque wrench can be fastened in the reverse direction and then rotated. Therefore, when fastening a screw using the torque wrench according to the present invention, the knob 26 is rotated to tighten the screw to a certain degree through the torque wrench driver bit, and then the rotation direction control knob 19 or the first body part 10 is rotated to rotate the torque wrench driver bit, thereby firmly fastening the screw. Furthermore, when removing the fastened screw, the rotation direction control knob 19 or the first body part 10 is rotated to release firm fastening, and then the knob 26 is rotated to completely remove the screw. Therefore, it is possible to first tighten the screw and finally firmly fasten the screw or to loosen the screw and completely remove the screw by using only a single torque wrench according to the present invention, even without the use of a separate hand driver tool.

Furthermore, a torque wrench for an implant procedure according to another embodiment of the present invention may be configured such that the above-described torque wrench driver bit 30 is integrally provided with the head portion 16 of the first body part 10.

Figure 4:
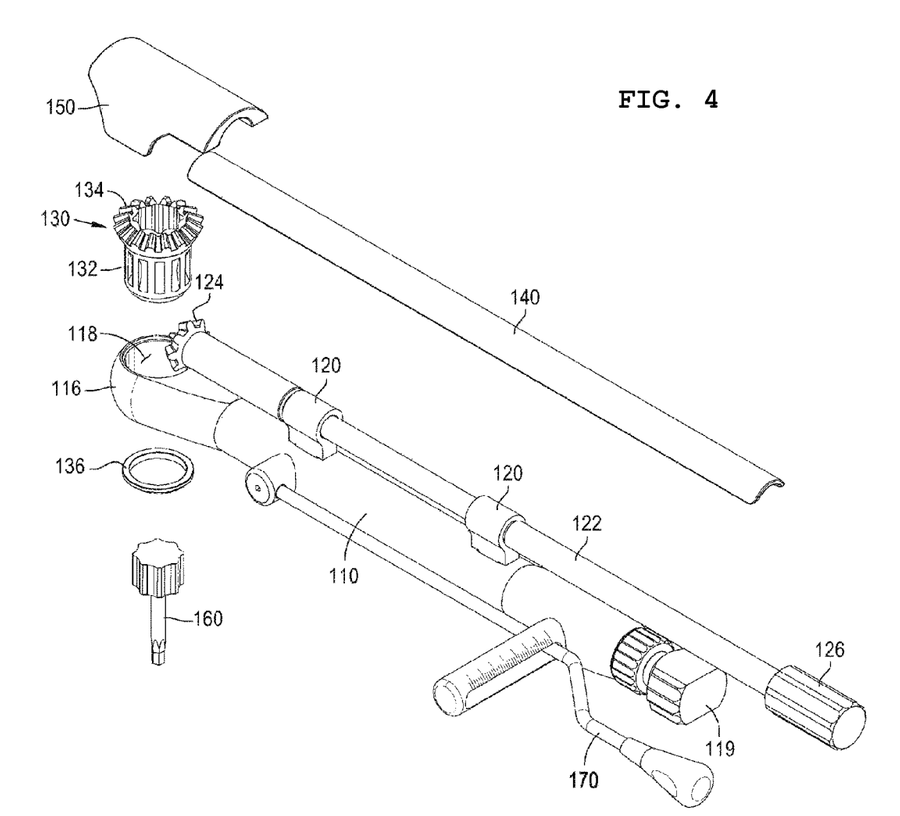
FIG. 4 is a perspective view illustrating a torque wrench according to another embodiment of the present invention.
Figure 5:
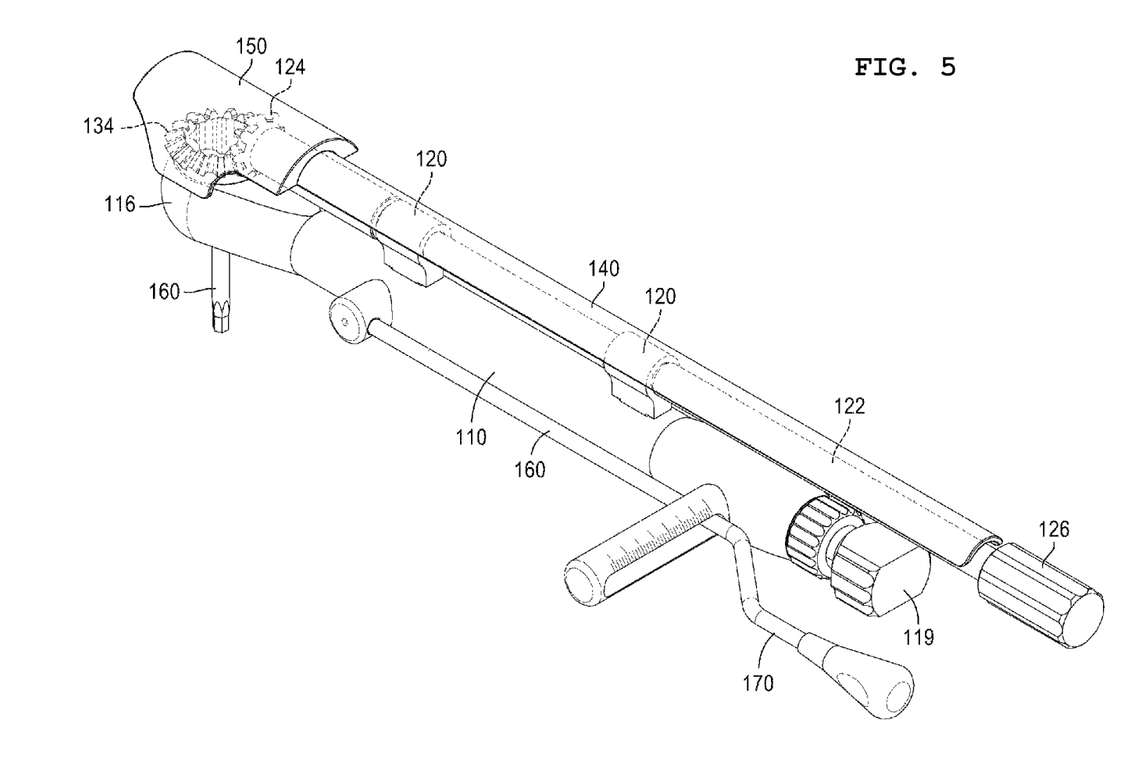
FIG. 5 is an exploded perspective view illustrating the torque wrench according to the embodiment of the present invention.

FIG. 4 is a perspective view illustrating a torque wrench according to another embodiment of the present invention, and FIG. 5 is an exploded perspective view illustrating the torque wrench according to the embodiment of the present invention. Referring to FIGS. 4 and 5, a first body part 110 includes a head portion 116 in which a fastening hole 118 is formed at one end thereof, a rotor 130 is integrally coupled to the fastening hole 118 of the head portion 116 so as to be rotatable, and a plurality of ratchet grooves 132 is formed in an outer surface of the rotor. Furthermore, a first gear is formed at an upper end of the rotor.

Furthermore, at least one second body part 120 is provided at one side of the first body part 110 at a predetermined length, and includes a coupling portion formed in a longitudinal direction thereof and to which a second shaft 122 is coupled. Preferably, the coupling portion may be in the form of a hollow portion. In FIGS. 4 and 5, two second body parts 120 are configured such that respective hollow portions thereof are arranged along longitudinal directions thereof, but the present invention is not limited thereto. Therefore, it should be interpreted as a concept including all forms as long as the second shaft can be coupled to the coupling portion of the second body part so as to be rotatable, regardless of the number, length and structure of the second body part.

The second shaft 122 is rotatably coupled to the coupling portion of the second body part 120, and is configured such that, in response to rotation of a knob 126 provided at the other end thereof, the second shaft transmits torque to the rotor 130 and/or a torque wrench driver bit 160 fastened to the fastening hole 118, through a second gear 124 formed at one end of the second shaft 122 and the first gear 134 engaged with the second gear 124. The rotor 130 may be rotatably coupled to the fastening hole 118 by a fixing piece 136. Preferably, the first gear 134 is formed at the upper end of the rotor 130, and the torque wrench driver bit 160 is fitted to the rotor 130. The first gear 134 is coupled to the second gear to transmit torque to the torque wrench driver bit 160. FIGS. 4 and 5 illustrate a structure in which torque is transmitted to the torque wrench driver bit 160 via the rotor 130. However, the present invention is not limited thereto. Therefore, it should be apparent for those skilled in the art that the first gear 134 can be modified and applied to the head portion 116 of the first body part 110 in various shapes and/or structures.

Referring to FIGS. 4 and 5, the present invention further includes a protective cover 150 protecting a portion where the first gear 134 and the second gear 124 are engaged with each other from being exposed externally. This is to prevent foreign substances or the like from being introduced into the gap between the gears during the procedure, resulting in malfunction or danger. The present invention further includes a shaft cover 140 provided at an upper side of the second body part 120 to prevent the second shaft 122 from being exposed externally.

Furthermore, as illustrated in FIGS. 1 to 5, the present invention may further include bar-shaped torque gauges 40 and 170 provided at one sides of the first body parts 10 and 110, respectively. In some cases, the bar-shaped torque gauges may be implemented in a curved shape.

While the specific embodiments of the invention have been described above in detail with reference to the drawings, the present invention should not be limited to specific structures of the embodiments. For example, the present invention may provide a torque wrench without the structure of the rotation direction control knob 19 in which the rotation direction of the torque wrench can be changed without changing the direction of fastening the torque wrench driver bit to the fastening hole. In another example, the structure of the fastening hole may be variously modified. Those skilled in the art will appreciate that various modifications, additions and substitutions are possible, without departing from the scope and spirit of the invention as disclosed in the accompanying claims. However, all of the simply modified or changed structures may be clearly included within the scope of rights of the present invention.

The invention claimed is:

1. A torque wrench for an implant procedure, the torque wrench comprising:
   a first body having a predetermined length and including a hollow portion formed in a longitudinal direction and a head portion where a fastening hole is formed at an end to which a torque wrench driver bit is coupled;
   at least one second body having a predetermined length, provided at one side of the first body, and including a coupling portion formed in the longitudinal direction;
   a first gear provided at an upper end of a rotor inserted into a fastening hole formed in the head portion, the rotor having a plurality of ratchet grooves formed in an outer surface thereof;
   a first shaft including a ratchet protrusion formed at one end thereof and configured to be inserted into the hollow portion of the first body such that the ratchet protrusion engages with the ratchet grooves of the rotor to transmit torque thereto;
   a second shaft rotatably coupled to the coupling portion of the second body, including a second gear provided at one end thereof and a knob provided at the other end thereof, and configured such that, in response to rotation of the knob, the second shaft transmits torque to the rotor and the torque wrench driver bit through the first gear engaged with the second gear; and
   a torque gauge provided at one side of the first body part.

2. The torque wrench of claim 1, wherein the first gear is rotatably provided at an upper side of the torque wrench driver bit or at one side of the head portion of the first body.

3. The torque wrench of claim 2, further comprising:
   a protective cover protecting a portion where the first gear and the second gear are engaged with each other from being exposed externally.

4. The torque wrench of claim 1, further comprising:
   a protective cover protecting a portion where the first gear and the second gear are engaged with each other from being exposed externally.

5. The torque wrench of claim 1, wherein the first gear and the second gear are directly engaged without any intervening gear.

6. A torque wrench for an implant procedure, the torque wrench comprising:
   a first body having a predetermined length and including a hollow portion formed in a longitudinal direction and a head portion where a fastening hole is formed at an end to which a torque wrench driver bit is coupled;

at least one second body having a predetermined length, provided at one side of the first body, and including a coupling portion formed in the longitudinal direction;

a first gear provided at an upper end of a rotor inserted into a fastening hole formed in the head portion, the rotor having a plurality of ratchet grooves formed in an outer surface thereof;

a first shaft including a ratchet protrusion formed at one end thereof and configured to be inserted into the hollow portion of the first body such that the ratchet protrusion engages with the ratchet grooves of the rotor to transmit torque thereto;

a second shaft rotatably coupled to the coupling portion of the second body, including a second gear provided at one end thereof and a knob provided at the other end thereof, and configured such that, in response to rotation of the knob, the second shaft transmits torque to the rotor and the torque wrench driver bit through the first gear engaged with the second gear; and a bar-shaped torque gauge provided at one side of the first body part, wherein the first body and the second body are aligned in parallel to each other along the longitudinal direction, and the first shaft and the second shaft are aligned in parallel to each other along the longitudinal direction.

7. The torque wrench of claim 6, wherein the first gear is rotatably provided at an upper side of the torque wrench driver bit or at one side of the head portion of the first body.

* * * * *